United States Patent [19]

Parg et al.

[11] 4,426,220
[45] Jan. 17, 1984

[54] DIPHENYL ETHERS, THEIR PREPARATION AND THEIR USE AS HERBICIDES

[75] Inventors: Adolf Parg, Bad Durkheim; Gerhard Hamprecht, Weinheim; Bruno Wuerzer, Otterstadt, all of Fed. Rep. of Germany

[73] Assignee: BASF Aktiengesellschaft, Fed. Rep. of Germany

[21] Appl. No.: 324,984

[22] Filed: Nov. 25, 1981

[30] Foreign Application Priority Data

Dec. 5, 1980 [DE] Fed. Rep. of Germany ....... 3045805

[51] Int. Cl.³ .................... C07C 101/04; A01N 31/00
[52] U.S. Cl. .......................................... 71/98; 71/103; 71/105; 71/108; 71/115; 71/118; 560/9; 560/12; 560/13; 560/21; 560/27; 560/39; 562/426; 562/432; 562/430; 562/435; 562/444; 260/465 E
[58] Field of Search ................... 560/9, 12, 13, 21, 27, 560/39; 562/426, 432, 430, 435, 444; 260/465 E; 71/103, 98, 108, 115, 118, 105

[56] References Cited

U.S. PATENT DOCUMENTS

| 4,134,753 | 1/1979 | Horlein et al. | 562/435 |
| 4,263,041 | 4/1981 | Grove | 71/108 |
| 4,339,268 | 7/1982 | Theissen | 560/21 |

FOREIGN PATENT DOCUMENTS

| 30676 | 6/1981 | European Pat. Off. | 71/108 |
| 54-151943 | of 0000 | Japan . | |
| 1423376 | 2/1976 | United Kingdom | 71/116 |
| 2049675 | 12/1980 | United Kingdom | 71/116 |
| 2051038 | 1/1981 | United Kingdom | 71/116 |

*Primary Examiner*—James H. Reamer
*Attorney, Agent, or Firm*—Keil & Witherspoon

[57] ABSTRACT

Diphenyl ethers of the formula

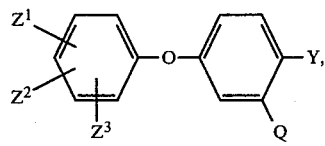

where $Z^1$, $Z^2$ and $Z^3$ independently of one another are each hyrogen, halogen, nitro, cyano, carboxyl, alkyl of 1 to 4 carbon atoms, or haloalkyl, alkoxy, haloalkoxy, alkylmercapto, haloalkylmercapto, alkylsulfinyl, haloalkylsulfinyl, alkylsulfonyl or haloalkylsulfonyl where alkyl is in each case of 1 to 4 carbon atoms, Y is hydrogen, halogen, cyano or nitro and Q is —CO—NA—OR¹, where A is hydrogen, alkyl of 1 to 4 carbon atoms, a metal ion or an unsubstituted or substituted ammonium ion and R¹ is carboxyalkyl, alkoxycarbonylalkyl or carbamylalkyl of not more than 10 carbon atoms, herbicides which contain these diphenyl ethers as active ingredients, and methods of controlling undesirable plant growth using these active ingredients.

9 Claims, No Drawings

DIPHENYL ETHERS, THEIR PREPARATION AND THEIR USE AS HERBICIDES

The present invention relates to diphenyl ethers, processes for their preparation, herbicides which contain these compounds as active ingredients, and a method of controlling undesirable plant growth using these active ingredients.

Numerous herbicidal active ingredients of the diphenyl ether category have been disclosed in the literature, for example 2-chloro-4-trifluoromethyl-3'-carbamyl-4'-nitrodiphenyl ether (Japanese Preliminary Published Application No. 79/151,943), diphenyl ether-oxime derivatives (German Laid-Open Application DOS No. 2,837,857) and the sodium salt of 2-chloro-4-trifluoromethyl-3'-carboxy-4'-nitrodiphenyl ether, which is especially used for controlling weeds in soybeans (German Laid-Open Application DOS No. 2,311,638).

We have found that diphenyl ethers of the formula I

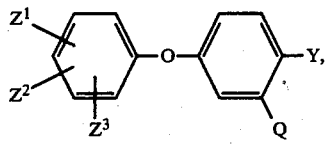

(I)

where $Z^1$, $Z^2$ and $Z^3$ independently of one another are each hydrogen, halogen, nitro, cyano, carboxyl, alkyl of 1 to 4 carbon atoms, or haloalkyl, alkoxy, haloalkoxy, alkylmercapto, haloalkylmercapto, alkylsulfinyl, haloalkylsulfinyl, alkylsulfonyl or haloalkylsulfonyl where alkyl is in each case of 1 to 4 carbon atoms, Y is hydrogen, halogen, cyano or nitro and Q is —CO—NA—OR$^1$, where A is hydrogen, alkyl of 1 to 4 carbon atoms, a metal ion or an unsubstituted or substituted ammonium ion and $R^1$ is carboxylalkyl, alkoxycarbonylalkyl or carbamylalkyl of not more than 10 carbon atoms, have a very good herbicidal activity and, depending on the formulation and dosage, have a selective herbicidal action and can be used for temporary total control of herbaceous plants.

In formula I, $Z^1$, $Z^2$ and $Z^3$ independently of one another are each hydrogen, halogen, such as fluorine, chlorine, bromine or iodine, nitro, cyano, carboxyl, alkyl of 1 to 4 carbon atoms, such as methyl, ethyl, n-propyl, i-propyl, n-butyl or tert.-butyl, or haloalkyl, alkoxy, haloalkoxy, alkylmercapto, haloalkylmercapto, alkylsulfinyl, haloalkylsulfinyl, alkylsulfonyl or haloalkylsulfonyl where alkyl is of 1 to 4 carbon atoms in each case, such as trifluoromethyl, difluoromethyl, fluoromethyl, trichloromethyl, dichloromethyl, chloromethyl, difluorochloromethyl, 1-chloroethyl, 2-chloroethyl, 1-fluoroethyl, 2-fluoroethyl, 2,2,2-trichloroethyl, 2,2,2-trifluoroethyl, 1,1,2,2-tetrafluoroethyl, 1,1,2-trifluoro-2-chloroethyl, 1,1,2,2,2-pentafluoroethyl, methoxy, ethoxy, n-propoxy, i-propoxy, tert.-butoxy, trichloromethoxy, trifluoromethoxy, 1-chloroethoxy, 2-chloroethoxy, 1-fluoroethoxy, 2-fluoroethoxy, 2,2,2-trichloroethoxy, 2,2,2-trifluoroethoxy, 1,1,2,2-tetrafluoroethoxy, 1,1,2,2,2-pentafluoroethoxy, methylmercapto, ethylmercapto, trichloromethylmercapto, trifluoromethylmercapto, methylsulfinyl, ethylsulfinyl, methylsulfonyl, ethylsulfonyl, trifluoromethylsulfinyl or trifluoromethylsulfonyl; Y is hydrogen, halogen, such as chlorine or bromine, cyano or nitro; and Q is —CO—NA—OR$^1$, where A is hydrogen, alkyl of 1 to 4 carbon atoms, in particular methyl or ethyl, or a metal ion or unsubstituted or substituted ammonium ion, for example a trialkylammonium ion or the unsubstituted ammonium ion, and especially the sodium or potassium ion, and $R^1$ is carboxyalkyl of the formula —(CHR$^2$)$_n$—COOH, where $R^2$ is hydrogen, methyl, ethyl or propyl and n is 1, 2 or 3, or $R^1$ is alkoxycarbonylalkyl of the formula —(CHR$^2$)$_n$—COOR$^3$, where $R^2$ is hydrogen, methyl, ethyl or propyl, n is 1, 2 or 3 and $R^3$ is alkyl of 1 to 20 carbon atoms, in particular of 1 to 3 carbon atoms, such as methyl, ethyl or propyl, or is a phenyl ring which is unsubstituted or substituted by halogen, alkyl of 1 to 4 carbon atoms, such as methyl or ethyl, haloalkyl of 1 to 4 carbon atoms, such as trifluoromethyl, or cyano, or $R^1$ is carbamylalkyl of the Formula —(CHR$^2$)$_n$—CO—NR$^4$R$^5$, where $R^2$ is hydrogen, methyl, ethyl or propyl, n is 1, 2 or 3 and $R^4$ and $R^5$ are identical or different and each is hydrogen, methyl, ethyl or a phenyl ring which is unsubstituted or substituted by halogen, alkyl of 1 to 4 carbon atoms, such as methyl or ethyl, haloalkyl of 1 to 4 carbon atoms, such as trifluoromethyl, or cyano.

The substituents $Z^1$, $Z^2$ and $Z^3$ are preferably in the 2-, 4- and 6-, or 3-, 4- and 6-, or 3-, 4- and 5-positions on the phenyl ring.

Preferred diphenyl ethers are the compounds of the formula I where $Z^1$, $Z^2$ and $Z^3$ are hydrogen or, in the 2-, 4- and 6-, or 3-, 4- and 6-, or 3-, 4- and 5-positions on the phenyl ring, independently of one another are each halogen or haloalkyl or haloalkylmercapto, each of 1 to 4 carbon atoms, Y is hydrogen, halogen or nitro and Q is —CO—NA—OR$^1$, where A is hydrogen or alkyl of 1 to 4 carbon atoms and $R^1$ is carboxyalkyl, alkoxycarbonylalkyl or carbamylalkyl of not more than 6 carbon atoms, and the compounds of the formula I where $Z^1$, $Z^2$ and $Z^3$ are hydrogen or, in the 2-, 4- and 6-, or 3-, 4- and 5-positions, independently of one another are each halogen or haloalkyl of 1 to 4 carbon atoms, Y is hydrogen or nitro and Q is —CO—NA—OR$^1$, where A is hydrogen and $R^1$ is alkoxycarbonylalkyl or carbamylalkyl of not more than 6 carbon atoms.

The compounds of the formula I can be prepared by the following processes:

In process (a), an acid chloride of the general formula II

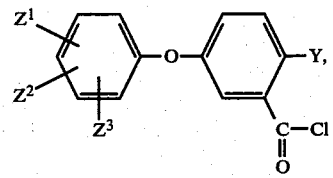

(II)

where $Z^1$, $Z^2$, $Z^3$ and Y have the above meanings, is reacted, continuously or batchwise, with not less than the equimolar amount of an O-substituted hydroxylamine of the general formula III $$H_2N-O-R^1$$ (III)

where $R^1$ has the above meanings, in an inert organic solvent, in the presence or absence of an acid acceptor, at from $-10°$ to $+120°$ C. and under atmospheric or superatmospheric pressure, to give a compound of the formula

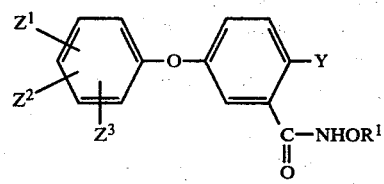

In process (b), a hydroxamic acid of the general formula IV

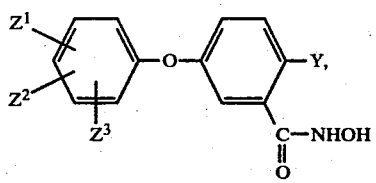
(IV)

where $Z^1$, $Z^2$, $Z^3$ and Y have the above meanings, is reacted, continuously or batchwise, with not less than the equimolar amount of a halogen compound of the general formula V Hal—$R^1$          (V), where $R^1$ has the above meanings and Hal is halogen, in an inert organic solvent, in the presence or absence of water and in the presence of an acid acceptor, especially sodium hydroxide or potassium hydroxide, at from 0° to 150° C. and under atmospheric or superatmospheric pressure, to give a compound of the formula

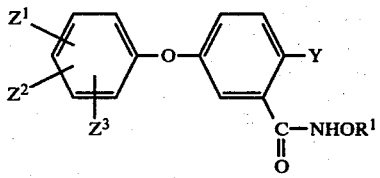

In process (c), a hydroxamic acid of the formula VI

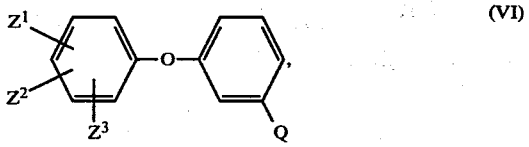
(VI)

where $Z^1$, $Z^2$ and $Z^3$ have the above meanings and Q is —CO—NA—O—$R^1$, where A is hydrogen and $R^1$ has the meanings given in claim 1, is nitrated, continuously or batchwise, with the equivalent amount of a nitrating mixture consisting of concentrated nitric acid or alkali metal nitrate and concentrated sulfuric acid, in the presence or absence or an organic solvent (acetic acid, acetic anhydride or dichloroethane), at from —10° to +15° C. and under atmospheric or superatmospheric pressure, to give a compound of the formula

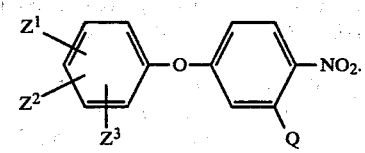

Process (a) can be represented by the following equation:

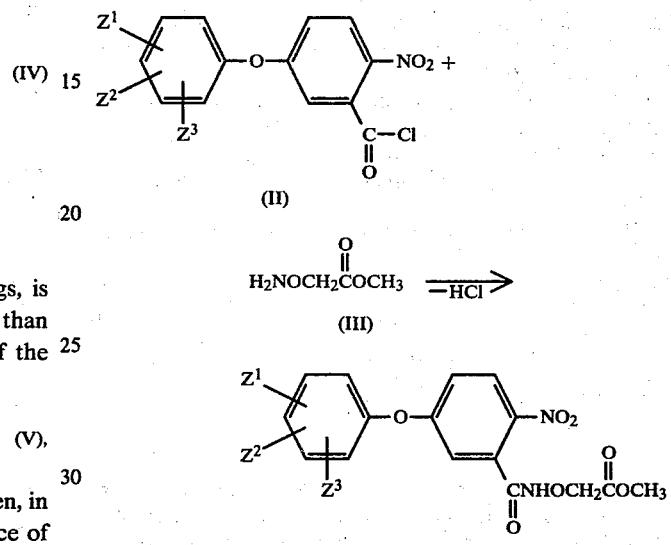

The starting substances are used in an approximately stoichiometric ratio, ie. from 0.9 to 1.1 moles of (III) are employed per mole of (II). If necessary, an acid acceptor can be added to bring the reaction to completion, in which case the amine III can also assume this function. The process is advantageously carried out by a method in which a solution of the acid chloride II at from —10° to +120° C., preferably from 0° to 60° C., in an organic solvent is run into a solution of the amine III in an inert organic solvent at the same time as the equimolar amount of an acid acceptor. To bring the reaction to completion, the mixture is stirred at from 0° to 60° C. for from 0.5 to 48 hours, preferably from 2 to 12 hours. The reaction mixture is concentrated, and the desired end product can be isolated by precipitating or crystallizing the residue or by stirring the residue with water; if necessary, it can be purified by chromatography.

Process (b) can be represented by the following equation:

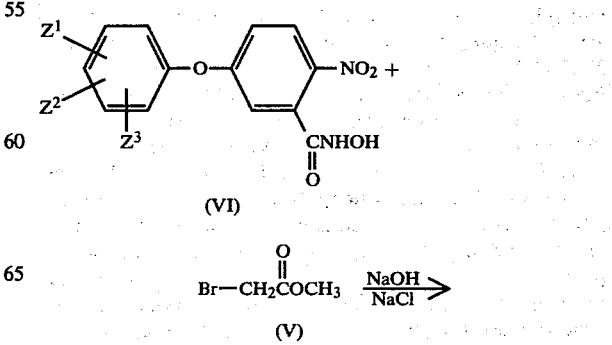

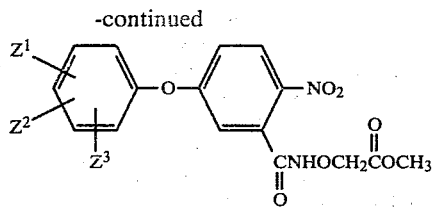

The starting substances can be used in the stoichiometric ratio, but an excess of not more than 50% of starting substance V, based on IV, is preferred. The process is advantageously carried out by preparing a mixture of the hydroxamic acid, the halogen component V and the acid acceptor in an organic solvent, in the presence or absence of water. A preferred acid acceptor is potassium hydroxide or sodium hydroxide, in from 1 to 1.5 times the molar amount, based on starting substance IV. The reaction mixture is stirred at from 0° to 150° C., preferably from 20° to 120° C., for from 0.5 to 48 hours, preferably from 2 to 12 hours. It is concentrated, and the desired end product can be isolated by precipitating, crystallizing or extracting the residue; if necessary, it can be purified by chromatography.

Process (c) can be represented by the following equation:

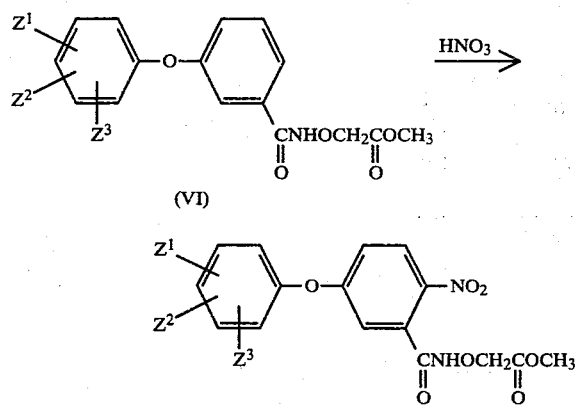

A solution of the starting substance VI, preferably in acetic anhydride or dichloroethane, is nitrated with the stoichiometric amount of concentrated acid or alkali metal nitrate (potassium nitrate) in the presence of from 1 to 10 times moles of concentrated sulfuric acid per mole of nitrating agent, at from −10° to +15° C., preferably from −5° to +5° C., in the course of from 0.5 to 8 hours, in particular from 1 to 4 hours. The mixture can then be stirred at from 15° to 25° C. for from 2 to 8 hours in order to bring the reaction to completion. Working up is effected by first stirring the reaction mixture into ice/water and then isolating the end product by extraction or filtration with suction; this product can be purified by reprecipitation or recrystallization, or, if necessary, by chromatography.

The starting substances are employed in an approximately stoichiometric ratio, ie. using from 0.9 to 1.1 moles of starting substance VIII per mole of VII. The process is advantageously carried out by stirring a solution of the starting substances VIII and VII in an organic solvent at from 20° to 150° C., preferably from 60° to 120° C., for from 0.5 to 48 hours, in particular from 2 to 12 hours. If necessary, the water of reaction can be removed from the system with the aid of an entraining agent (toluene), via a water separator. The reaction mixture is then concentrated. The end product can be isolated by precipitation, crystallization or extraction; if necessary, it can be purified by chromatography.

Organic solvents which are inert under the particular reaction conditions are used for processes (a), (b) and (c). Examples of suitable solvents are: halohydrocarbons, in particular chlorohydrocarbons, eg. tetrachloroethylene, 1,1,2,2- or 1,1,1,2-tetrachloroethane, dichloropropane, methylene chloride, dichlorobutane, chloroform, chloronaphthalene, dichloronaphthalene, carbon tetrachloride, 1,1,1- or 1,1,2-trichloroethane, trichloroethylene, pentachloroethane, o-, m- or p-difluorobenzene, 1,2-dichloroethane, 1,1-dichloroethane, 1,2-cis-dichloroethylene, chlorobenzene, fluorobenzene, bromobenzene, iodobenzene, o-, p- or m-dichlorobenzene, o-, p- or m-dibromobenzene, o-, m- or p-chlorotoluene and 1,2,4-trichlorobenzene; ethers, eg. ethyl propyl ether, methyl tert.-butyl ether, n-butyl ethyl ether, di-n-butyl ether, diisobutyl ether, diisoamyl ether, diisopropyl ether, anisole, phenetole, cyclohexyl methyl ether, diethyl ether, ethylene glycol dimethyl ether, tetrahydrofuran, dioxane, thioanisole and $\beta,\beta'$-dichlorodiethyl ether; nitrohydrocarbons eg. nitromethane, nitroethane, nitrobenzene, o-, m- or p-chloronitrobenzene and o-nitrotoluene; nitriles, eg. acetonitrile, butyronitrile, isobutyronitrile, benzonitrile and m-chlorobenzonitrile; aliphatic, cycloaliphatic or aromatic hydrocarbons eg. heptane, pinane, nonane, o-, m- or p-cymene, gasoline fractions with a boiling range of from 70° to 190° C., cyclohexane, methylcyclohexane, decalin, petroleum ether, hexane, naphtha, 2,2,4-trimethylpentane, 2,2,3-trimethylpentane, 2,3,3-trimethylpentane and octane; esters, eg. ethyl acetate, ethyl acetoacetate, and isobutyl acetate; amides, eg. formamide, methylformamide and dimethylformamide; ketones, eg. acetone and methyl ethyl ketone; and corresponding mixtures. From 100 to 2000% by weight, preferably from 200 to 700% by weight, based on the starting substances, of the solvent is advantageously used.

If the reaction is carried out in the presence of water (process b), suitable organic solvents are, in particular, alcohols, such as methanol, ethanol, propanol, isopropanol, butanols, hexanols, glycol, cyclohexanol, cyclopentanol and cycloheptanol.

All the conventional acid acceptors can be used. Preferred acceptors include tertiary amines, alkaline earth metal compounds, ammonium compounds and alkali metal compounds, and corresponding mixtures. Zinc compounds can also be used. Examples of suitable basic compounds are: potassium hydroxide, sodium hydroxide, potassium carbonate, sodium carbonate, lithium hydroxide, lithium carbonate, sodium bicarbonate, potassium bicarbonate, calcium hydroxide, calcium oxide, barium oxide, magnesium hydroxide, magnesium oxide, barium hydroxide, calcium carbonate, magnesium carbonate, magnesium bicarbonate, magnesium acetate, zinc hydroxide, zinc oxide, zinc carbonate, zinc bicarbonate, zinc acetate, sodium formate, sodium acetate, trimethylamine, triethylamine, tripropylamine, triisopropylamine, tributylamine, triisobutylamine, tri-sec.-butylamine, tri-tert.-butylamine, tribenzylamine, tricyclohexylamine, triamylamine, diisopropylethylamine, trihexylamine, N,N-dimethylaniline, N,N-diethylaniline, N,N-dipropylaniline, N,N-dimethyltoluidine, N,N-diethyltoluidine, N,N-dipropyltoluidine, N,N-dipropyltoluidine, N,N-dimethyl-p-aminopyridine, N,N-diethyl-p-aminopyridine, N,N-dipropyl-p- aminopyridine, N-methylpyrrolidone, N-ethylpyrrolidone, N-methylpiperidine, N-ethylpiperidine, N-methylpyrrolidine, N-ethylpyrrolidine, N-methylimidazole, N-ethylimidazole, N-methylpyrrole, N-ethylpyrrole, N-methylmorpholine, N-methylhexamethyleneimine, N-ethylhexamethyleneimine, pyridine, quinoline, α-picoline, β-picoline, γ-picoline, isoquinoline, pyrimidine, acridine, N,N,N',N'-tetramethylethylenediamine, N,N,N',N'-tetraethylethylenediamine, quinoxaline, quinazoline, N-propyldiisopropylamine, N,N'-dimethylcyclohexylamine, 2,6-lutidine, 2,4-lutidine, trifurylamine and triethylenediamine.

The starting compounds are prepared by methods which are known from the literature. First, the acid chlorides of the general formula II are prepared from the corresponding acids by means of chlorinating agents by a generally conventional procedure. The acids can in turn be prepared, for example, by the processes disclosed in U.S. Pat. No. 4,031,131 and U.S. Pat. No. 4,002,662.

The hydroxamic acids can be prepared by the methods described in Houben-Weyl, Methoden der organischen Chemie, Volume X/4, pages 10 and 12, Georg-Thieme-Verlag, Stuttgart, 1968. O-Alkylated hydroxylamines of the general formula III can be prepared by the process described in Houben-Weyl, Methoden der organischen Chemie, Volume X/1, page 1182, Georg-Thieme-Verlag, Stuttgart, 1971.

Branched alkyl and alkane-carboxylic acid radicals exist in various enantiomeric forms and as racemates. All the enantiomeric forms by themselves and as mixtures in any desired ratio, and especially the racemate, are embraced by the present description.

The Example which follows illustrates the preparation of the compounds of the formula I. Parts by weight bear the same relation to parts by volume as that of the kilogram to the liter.

EXAMPLE 16.7 parts by weight of methyl 2-bromopropionate and 4 parts by weight of sodium hydroxide are added, in succession, to a solution of 37.6 parts by weight of 3-(2'-chloro-4'-trifluoromethylphenoxy)-6-nitro-benzhydroxamic acid in 250 parts by volume of ethanol and 70 parts by volume of water at room temperature. The reaction mixture is refluxed, subsequently stirred for 2 hours, cooled, and concentrated to dryness under reduced pressure. The residue is taken up in ether and the organic phase is extracted with water, dried with magnesium sulfate and concentrated under reduced pressure. Chromatography over silica gel using a 30/70 mixture of acetone and toluene gives 20 parts by weight (=43% of theory) of the compound of the formula

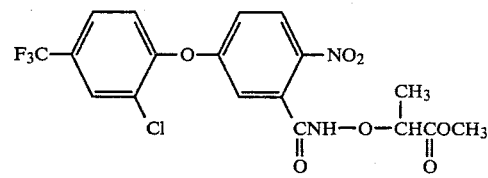

Melting point: 119° C.–122° C. (recrystallized from diisopropyl ether).

The following compounds of the formula I, for example, can be prepared by a similar method.

| No. | $Z^1$, $Z^2$, $Z^3$ | Y | Q | m.p. [°C.]; $n_d^{25}$; Wavelength of a band in the infrared spectrum |
|---|---|---|---|---|
| 2 | 2-Chloro-4-trifluoromethylphenoxy | H | —CO—NH—OCH$_2$COOCH$_3$ | 1.5422 |
| 3 | 2-Chloro-4-trifluoromethylphenoxy | " | —CO—NHOCH(CH$_3$)—COOCH$_3$ | 1.5372 |
| 4 | 2-Chloro-4-trifluoromethylphenoxy | " | —CO—NHOCH(CH$_3$)—COOH | |
| 5 | 2-Chloro-4-trifluoromethylphenoxy | " | —CO—NHOCH(CH$_3$)—COOC$_{12}$H$_{25}$ | |
| 6 | 2-Chloro-4-trifluoromethylphenoxy | NO$_2$ | —CO—NHOCH$_2$COOCH$_3$ | 112–116 |
| 7 | 2-Chloro-4-trifluoromethylphenoxy | " | —CO—NHO—CH(C$_2$H$_5$)COOCH$_3$ | |
| 8 | 2-Chloro-4-trifluoromethylphenoxy | " | —CO—NHO—CH(CH$_3$)—COOH | 1.5372 |
| 9 | 2-Chloro-4-trifluoromethylphenoxy | " | —CO—N(Na)—O—CH(CH$_3$)—COOCH$_3$ | $\gamma_{CO} = 1740$ cm$^{-1}$ |

-continued

| No. | $Z^3$ | Y | Q | m.p. [°C.]; $n_d^{25}$; Wavelength of a band in the infrared spectrum |
|---|---|---|---|---|
| 10 | 2-Chloro-4-tri-fluoromethylphenoxy | " | $-CO-NH-O-CH(CH_3)-CO-NHCH_3$ | |
| 11 | 2,4-Dichlorophenoxy | " | $-CO-NH-OCH_2-COOCH_3$ | |
| 12 | " | " | $-CO-NHO-CH(CH_3)-COOCH_3$ | |
| 13 | " | " | $-CO-NHOCH(C_2H_5)-COOCH_3$ | |

The diphenyl ethers of the formula I may be applied for instance in the form of directly sprayable solutions, powders, suspensions (including high-percentage aqueous, oily or other suspensions), dispersions, emulsions, oil dispersions, pastes, dusts, broadcasting agents, or granules by spraying, atomizing, dusting, broadcasting or watering. The forms of application depend entirely on the purpose for which the agents are being used; in any case they should ensure as fine a distribution of the active ingredient as possible.

For the preparation of solutions, emulsions, pastes and oil dispersions to be sprayed direct, mineral oil fractions of medium to high boiling point, such as kerosene or diesel oil, further coal-tar oils, and oils of vegetable or animal origin, aliphatic, cyclic and aromatic hydrocarbons such as benzene, toluene, xylene, paraffin, tetrahydronaphthalene, alkylated naphthalenes and their derivatives such as methanol, ethanol, propanol, butanol, chloroform, carbon tetrachloride, cyclohexanol, cyclohexanone, chlorobenzene, isophorone, etc., and strongly polar solvents such as dimethylformamide, dimethylsulfoxide, N-methylpyrrolidone, water, etc. are suitable.

Aqueous formulations may be prepared from emulsion concentrates, pastes, oil dispersions or wettable powders by adding water. To prepare emulsions, pastes and oil dispersions the ingredients as such or dissolved in an oil or solvent may be homogenized in water by means of wetting or dispersing agents, adherents or emulsifiers. Concentrates which are suitable for dilution with water may be prepared from active ingredient, wetting agent, adherent, emulsifying or dispersing agent and possibly solvent or oil.

Examples of surfactants are: alkali metal, alkaline earth metal and ammonium salts of ligninsulfonic acid, naphthalenesulfonic acids, phenolsulfonic acids, alkylaryl sulfonates, alkyl sulfates, and alkyl sulfonates, alkali metal and alkaline earth metal salts of dibutylnaphthalenesulfonic acid, lauryl ether sulfate, fatty alcohol sulfates, alkali metal and alkaline earth metal salts of fatty acids, salts of sulfated hexadecanols, heptadecanols, and octadecanols, salts of sulfated fatty alcohol glycol ethers, condensation products of sulfonated naphthalene and naphthalene derivatives with formaldehyde, condensation products of naphthalene or naphthlanesulfonic acids with phenol and formaldehyde, polyoxyethylene octylphenol ethers, ethoxylated isooctylphenol, ethoxylated octylphenol and ethoxylated nonylphenol, alkylphenol, polyglycol ethers, tributylphenyl polyglycol ethers, alkylaryl polyether alcohols, isotridecyl alcohol, fatty alcohol ethylene oxide condensates, ethoxylated castor oil, polyoxyethylene alkyl ethers, ethoxylated polyoxypropylene, lauryl alcohol polyglycol ether acetal, sorbitol esters, lignin, sulfite waste liquors and methyl cellulose.

Powders, dusts and broadcasting agents may be prepared by mixing or grinding the active ingredients with a solid carrier.

Granules, e.g., coated, impregnated or homogeneous granules, may be prepared by bonding the active ingredients to solid carriers. Examples of solid carriers are mineral earths such as silicic acid, silica gels, silicates, talc, kaolin, Attaclay, limestone, lime, chalk, bole, loess, clay, dolomite, diatomaceous earth, calcium sulfate, magnesium sulfate, magnesium oxide, ground plastics, fertilizers such as ammonium sulfate, ammonium phosphate, ammonium nitrate, and ureas, and vegetable products such as grain flours, bark meal, wood meal, and nutshell meal, cellulosic powders, etc.

The formulations contain from 0.1 to 95, and preferably 0.5 to 90, % by weight of active ingredient.

Examples of formulations are given below.

I. 90 parts by weight of compound no. 1 is mixed with 10 parts by weight of N-methyl-α-pyrrolidone. A mixture is obtained which is suitable for application in the form of very fine drops.

II. 10 parts by weight of compound no. 2 is dissolved in a mixture consisting of 90 parts by weight of xylene, 6 parts by weight of the adduct of 8 to 10 moles of ethylene oxide with 1 mole of oleic acid-N-monoethanolamide, 2 parts by weight of the calcium salt of dodecylbenzenesulfonic acid, and 2 parts by weight of the adduct of 40 moles of ethylene oxide with 1 mole of castor oil.

III. 20 parts by weight of compound no. 8 is dissolved in a mixture consisting of 60 parts by weight of cyclohexanone, 30 parts by weight of isobutanol, 5 parts by weight of the adduct of 7 moles of ethylene oxide with 1 mole of isooctylphenol, and 5 parts by weight of the adduct of 40 moles of ethylene oxide with 1 mole of castor oil.

IV. 20 parts by weight of compound no. 9 is dissolved in a mixture consisting of 25 parts by weight of cyclohexanol, 65 parts by weight of a mineral oil fraction having a boiling point between 210° and 280° C., and 10 parts by weight of the adduct of 40 moles of ethylene oxide with 1 mole of castor oil. By pouring the solution into 100,000 parts by weight of water and uniformly distributing it therein, an aqueous dispersion is obtained containing 0.02% by weight of the active ingredient.

V. 80 parts by weight of compound no. 2 is well mixed with 3 parts by weight of the sodium salt of diisobutylnaphthalene-α-sulfonic acid, 10 parts by weight of the sodium salt of a lignin-sulfonic acid obtained from a sulfite waste liquor, and 7 parts by weight of powdered silica gel, and triturated in a hammer mill.

VI. 5 parts by weight of compound no. 3 is intimately mixed with 95 parts by weight of particulate kaolin. A dust is obtained containing 5% by weight of the active ingredient.

VII. 30 parts by weight of compound no. 9 is intimately mixed with a mixture consisting of 92 parts by weight of powdered silica gel and 8 parts by weight of paraffin oil which has been sprayed onto the surface of this silica gel. A formulation of the active ingredient is obtained having good adherence.

VIII. 20 parts of compound no. 13 is intimately mixed with 2 parts of the calcium salt of dodecylbenzenesulfonic acid, 8 parts of a fatty alcohol polyglyol ether, 2 parts of the sodium salt of a phenolsulfonic acid-urea-formaldehyde condensate and 68 parts of a paraffinic mineral oil. A stable oily dispersion is obtained.

A formulation of the active ingredient in emulsifiable oil is particularly important, as this results in a general increase in effectiveness in combating herbaceous plant growth on leaf treatment.

Application rates may vary from 0.01 to 10.0 kg/ha and more of active ingredient. They depend on the objective and the growth stage of the unwanted plants. Preferred rates are from 0.05 to 3.0 kg/ha.

If certain crop plants tolerate, on leaf treatment, the active ingredients less well, application techniques may be used in which the agents are sprayed from suitable equipment in such a manner that the leaves of sensitive crop plants are if possible not touched, and the agents reach the soil or the unwanted plants growing beneath the crop plants (post-directed, lay-by treatment).

In view of the many application methods possible, the herbicides according to the invention may be used in a very wide range of crops for removing unwanted plants.

| Botanical name | Common name |
|---|---|
| Allium cepa | onions |
| Ananas comosus | pineapples |
| Arachis hypogaea | peanuts (groundnuts) |
| Asparagus officinalis | asparagus |
| Avena sativa | oats |
| Beta vulgaris spp. altissima | sugarbeets |
| Beta vulgaris spp. rapa | fodder beets |
| Beta vulgaris spp. esculenta | table beets, red beets |
| Brassica napus var. napus | rape seed |
| Brassica napus var. napobrassica | |
| Brassica napus var. rapa | turnips |
| Brassica rapa var. silvestris | |
| Camellia sinensis | tea plants |
| Carthamus tinctorius | safflower |
| Carya illinoinensis | pecan trees |
| Citrus limon | lemons |
| Citrus maxima | grapefruits |
| Citrus reticulata | mandarins |
| Citrus sinensis | orange trees |
| Coffea arabica (Coffea canephora, Coffea liberica) | coffee plants |
| Cucumis melo | melons |
| Cucumis sativus | cucumbers |
| Cynodon dactylon | Bermudagrass |
| | in turf and lawns |
| Daucus carota | carrots |
| Elais guineensis | oil palms |
| Fragaria vesca | strawberries |
| Glycine max | soybeans |
| Gossypium hirsutum (Gossypium arboreum Gossypium herbaceum Gossypium vitifolium) | cotton |
| Helianthus annuus | sunflowers |
| Helianthus tuberosus | |
| Hevea brasiliensis | rubber plants |
| Hordeum vulgare | barley |
| Humulus lupulus | hops |
| Ipomoea batatas | sweet potatoes |
| Juglans regia | walnut trees |
| Lactuca sativa | lettuce |
| Lens culinaris | lentils |
| Linum usitatissimum | flax |
| Lycopersicon lycopersicum | tomatoes |
| Malus spp. | apple trees |
| Manihot esculenta | cassava |
| Medicago sativa | alfalfa (lucerne) |
| Mentha piperita | peppermint |
| Musa spp. | banana plants |
| Nicothiana tabacum (N. rustica) | tobacco |
| Olea europaea | olive trees |
| Oryza sativa | rice |
| Panicum miliaceum | |
| Phaseolus lunatus | limabeans |
| Phaseolus mungo | mungbeans |
| Phaseolus vulgaris | snapbeans, green beans, dry beans |
| Pennisetum glaucum | |
| Petroselinum crispum | parsley |
| spp. tuberosum | |
| Picea abies | Norway spruce |
| Abies alba | fir trees |
| Pinus spp. | pine trees |
| Pisum sativum | English peas |
| Prunus avium | cherry trees |
| Prunus domestica | plum trees |
| Prunus dulcis | almond trees |
| Prunus persica | peach trees |
| Pyrus communis | pear trees |
| Ribes sylvestre | redcurrants |
| Ribes uva-crispa | gooseberries |
| Ricinus communis | castor-oil plants |
| Saccharum officinarum | sugar cane |
| Secale cereale | rye |
| Sesamum indicum | sesame |
| Solanum tuberosum | Irish potatoes |
| Sorghum bicolor (s. vulgare) | sorghum |
| Sorghum dochna | |
| Spinacia oleracea | spinach |
| Theobroma cacao | cacao plants |
| Trifolium pratense | red clover |
| Triticum aestivum | wheat |
| Vaccinium corymbosum | blueberries |
| Vaccinium vitis-idaea | cranberries |
| Vicia faba | tick beans |
| Vigna sinensis (V. unguiculata) | cow peas |
| Vitis vinifera | grapes |
| Zea mays | Indian corn, sweet corn, maize |

To increase the spectrum of action and to achieve synergistic effects, the novel diphenyl ethers may be mixed among themselves, or mixed and applied together with numerous representatives of other herbicidal or growth-regulating active ingredient groups. Examples of suitable mixture components are diazines, 4H-3,1-benzoxazine derivatives, benzothiadiazinones, 2,6-dinitroanilines, N-phenylcarbamates, thiolcarbamates, halocarboxylic acids, triazines, amides, ureas, other diphenyl ethers, triazinones, uracils, benzofuran derivatives, cyclohexane-1,3-dione derivatives, etc. A number of active ingredients which, when combined with the new compounds, give mixtures useful for widely varying applications are given below by way of example:

5-amino-4-chloro-2-phenyl-3(2H)-pyridazinone
5-amino-4-bromo-2-phenyl-3(2H)-pyridazinone
5-amino-4-chloro-2-cyclohexyl-3(2H)-pyridazinone
5-amino-4-bromo-2-cyclohexyl-3(2H)-pyridazinone
5-methylamino-4-chloro-2-(3-trifluoromethylphenyl)-3(2H)-pyridazinone
5-methylamino-4-chloro-2-(3-α,α,β,β-tetrafluoroethoxyphenyl)-3(2H)-pyridazinone
5-dimethylamino-4-chloro-2-phenyl-3(2H)-pyridazinone
4,5-dimethoxy-2-phenyl-3(2H)-pyridazinone
4,5-dimethoxy-2-cyclohexyl-3(2H)-pyridazinone
4,5-dimethoxy-2-(3-trifluoromethylphenyl)-3(2H)-pyridazinone
5-methoxy-4-chloro-2-(3-trifluoromethylphenyl)-3(2H)-pyridazinone
5-amino-4-bromo-2(3-methylphenyl)-3(2H)-pyridazinone
4,5-dimethoxy-2-(3-α,α,β-trifluoro-β-bromoethoxyphenyl)-3-(2H)-pyridazinone
3-(1-methylethyl)-1H-2,1,3-benzothiadiazin-4(3H)-one-2,2-dioxide and salts
3-(1-methylethyl)-8-chloro-1H-2,1,3-benzothiadiazin-4(3H)-one-2,2-dioxide and salts
3-(1-methylethyl)-8-fluoro-1H-2,1,3-benzothiadiazin-4(3H)-one-2,2-dioxide and salts
3-(1-methylethyl)-8-methyl-1H-2,1,3-benzothiadiazin-4(3H)-one-2,2-dioxide and salts
1-methoxymethyl-3-(1-methylethyl)-2,1,3-benzothiadiazin-4(3H)-one-2,2-dioxide
1-methoxymethyl-8-chloro-3-(1-methylethyl)-2,1,3-benzothiadiazin-4(3H)-one-2,2-dioxide
1-methoxymethyl-8-fluoro-3-(1-methylethyl)-2,1,3-benzothiadiazin-4(3H)-one-2,2-dioxide
1-cyano-8-chloro-3-(1-methylethyl)-2,1,3-benzothiadiazin-4(3H)-one-2,2-dioxide
1-cyano-8-fluoro-3-(1-methylethyl)-2,1,3-benzothiadiazin-4(3H)-one-2,2-dioxide
1-cyano-8-methyl-3-(1-methylethyl)-2,1,3-benzothiadiazin-4(3H)-one-2,2-dioxide
1-cyano-3-(1-methylethyl)-2,1,3-benzothiadiazin-4(3H)-one-2,2-dioxide
1-azidomethyl-3-(1-methylethyl)-2,1,3-benzothiadiazin-4(3H)-one-2,2-dioxide
3-(1-methylethyl)-1H-pyridino-[3,2-e]-2,1,3-thiadiazin-(4)-one-2,2-dioxide
N-(1-ethylpropyl)-2,6-dinitro-3,4-dimethylaniline
N-(1-methylethyl)-N-ethyl-2,6-dinitro-4-trifluoromethylaniline
N-n-propyl-N-β-chloroethyl-2,6-dinitro-4-trifluoromethylaniline
N-n-propyl-N-cyclopropylmethyl-2,6-dinitro-4-trifluoromethylaniline
N-bis-(n-propyl)-2,6-dinitro-3-amino-4-trifluoromethylaniline
N-bis-(n-propyl)-2,6-dinitro-4-methylaniline
N-bis-(n-propyl)-2,6-dinitro-4-methylsulfonylaniline
N-bis-(n-propyl)-2,6-dinitro-4-aminosulfonylaniline
bis-(β-chloroethyl)-2,6-dinitro-4-methylaniline
N-ethyl-N-(2-methylallyl)-2,6-dinitro-4-trifluoromethylaniline
3,4-dichlorobenzyl N-methylcarbamate
2,6-di-tert.butyl-4-methylphenyl N-methylcarbamate isopropyl N-phenylcarbamate
3-methoxyprop-2-yl N-3-fluorophenylcarbamate isopropyl N-3-chlorophenylcarbamate but-1-yn-3-yl N-3-chlorophenylcarbamate
4-chlorobut-2-yn-1-yl N-3-chlorophenylcarbamate
methyl N-3,4-dichlorophenylcarbamate methyl N-(4-aminobenzenesulfonyl)-carbamate
O-(N-phenylcarbamoyl)-propanone oxime
N-ethyl-2-(phenylcarbamoyl)-oxypropionic acid amide
3'-N-isopropylcarbamoyloxypropionanilide
ethyl-N-(3-(N'-phenylcarbamoyloxy)-phenyl)-carbamate methyl-N-(3-(N'-methyl-N'-phenylcarbamoyloxy)-phenyl)-carbamate
isopropyl-N-(3-(N'-ethyl-N'-phenylcarbamoyloxy)-phenyl)-carbamate
methyl-N-(3-(N'-3-methylphenylcarbamoyloxy)-phenyl)-carbamate
methyl-N-(3-(N'-4-fluorophenylcarbamoyloxy)-phenyl)-carbamate
methyl-N-(3-(N'-3-chloro-4-fluorophenylcarbamoyloxy)-phenyl)-carbamate
methyl-N-dichlorofluromethylsulfenyl-(3-(N'-dichlorofluoromethylsulfenyl-N'-phenylcarbamoyloxy)-phenyl)-carbamate
methyl-N-dichlorofluoromethylsulfenyl-(3-(N'-dichlorofluoromethylsulfenyl-N'-3-methylphenylcarbamoyloxy)-phenyl)-carbamate
ethyl-N-[3-N'-(3-chloro-4-fluorophenylcarbamoxyloxy)-phenyl]carbamate
ethyl-N-[3-N'-(3,4-difluorophenylcarbamoyloxy)-phenyl]-carbamate
methyl-N-[3-(N'-3,4-difluorophenylcarbamoyloxy)-phenyl]-carbamate
methyl N-3-(4'-fluorophenoxycarbonylamino)-phenylcarbamate
ethyl N-3-(2'-methylphenoxycarbonylamino)-phenylcarbamate
methyl N-3-(4'-fluorophenoxycarbonylamino)-phenylthiolcarbamate
methyl N-3-(2',4',5'-trimethylphenoxycarbonylamino)-phenylthiolcarbamate
methyl N-3-(phenoxycarbonylamino)-phenylthiolcarbamate
p-chlorobenzyl N,N-diethylthiolcarbamate
ethyl N,N-di-n-propylthiolcarbamate
n-propyl N,N-di-n-propylthiolcarbamate
2,3-dichloroallyl N,N-diisopropylthiolcarbamate
2,3,3-trichloroallyl N,N-diisopropylthiolcarbamate
3-methyl-5-isoxazolylmethyl N,N-diisopropylthiolcarbamate
3-ethyl-5-isoxazolylmethyl N,N-diisopropylthiolcarbamate
ethyl N,N-di-sec.-butylthiolcarbamate
benzyl N,N-di-sec.-butylthiolcarbamate
ethyl N-ethyl-N-cyclohexylthiolcarbamate
ethyl N-ethyl-N-bicyclo-[2.2.1]-heptylthiolcarbamate
S-(2,3-dichloroallyl)-(2,2,4-trimethylazetidine)-1-carbothiolate
S-(2,3,3-trichloroallyl)-(2,2,4-trimethylazetidine)-1-carbothiolate
S-ethylhexahydro-1-H-azepine-1-carbothiolate
S-benzyl-(3-methylhexahydro-1-H-azepine-1)-carbothiolate
S-benzyl-(2,3-dimethylhexahydro-1H-azepine-1)-carbothiolate
S-ethyl-(3-methylhexahydro-1-H-azepine-1)-carbothiolate n-propyl N-ethyl-N-n-butylthiolcarbamate
2-chloroallyl N,N-dimethyldithiocarbamate
N-methyldithiocarbamic acid, sodium salt
trichloroacetic acid, sodium salt
α,α-dichloropropionic acid, sodium salt
α,α-dichlorobutyric acid, sodium salt
α,α-β,β-tetrafluoropropionic acid, sodium salt
α-methyl-α,β-dichloropropionic acid, sodium salt
methyl α-chloro-β-(4-chlorophenyl)-propionate
methyl α,β-dichloro-β-phenylpropionate
benzamido oxyacetic acid
2,3,5-triiodobenzoic acid (salts, esters, amides)
2,3,6-trichlorobenzoic acid (salts, esters, amides)
2,3,5,6-tetrachlorobenzoic acid (salts, esters, amides)
2-methoxy-3,6-dichlorobenzoic acid (salts, esters, amides)
2-methoxy-3,5,6-trichlorobenzoic acid (salts, esters, amides)
3-amino-2,5,6-trichlorobenzoic acid (salts, esters, amides)
O,S-dimethyltetrachlorothioterephthalate
dimethyl-2,3,5,6-tetrachloroterephthalate
disodium 3,6-endoxohexahydrophthalate
4-amino-3,5,6-trichloropicolinic acid (salts)
ethyl 2-cyano-3-(N-methyl-N-phenyl)-aminoacrylate
isobutyl 2-[4-(4'-chlorophenoxy)-phenoxy]-propionate
methyl 2-[4-(2',4'-dichlorophenoxy)-phenoxy]-propionate
methyl 2-[4-(4'-trifluoromethylphenoxy)-phenoxy]-propionate
2-[4-(2'-chloro-4'-trifluorophenoxy)-phenoxy]-propionic acid, sodium salt
2-[4-(3',5'-dichloropyridyl-2-oxy)-phenoxy]-propionic acid, sodium salt
ethyl 2-(N-benzoyl-3,4-dichlorophenylamino)-propionate
methyl 2-(N-benzoyl-3-chloro-4-fluorophenylamino)-propionate
isopropyl 2-(N-benzoyl-3-chloro-4-fluorophenylamino)-propionate
ethyl 4-[4-(4'-trifluoromethyl-phenoxy)]-pentene-2-carboxylate
2-chloro-4-ethylamino-6-isopropylamino-1,3,5-triazine
2-chloro-4-ethylamino-6-(amino-2'-propionitrile)-1,3,5-triazine
2-chloro-4-ethylamino-6-(2-methoxypropyl)-2-amino-1,3,5-triazine
2-chloro-4-ethylamino-6-butyn-1-yl-2-amino-1,3,5-triazine
2-chloro-4,6-bisethylamino-1,3,5-triazine
2-chloro-4,6-bisisopropylamino-1,3,5-triazine
2-chloro-4-isopropylamino-6-cyclopropylamino-1,3,5-triazine
2-azido-4-methylamino-6-isopropylamino-1,3,5-triazine
2-methylthio-4-ethylamino-6-isopropylamino-1,3,5-triazine
2-methylthio-4-ethylamino-6-tert.butylamino-1,3,5-triazine
2-methylthio-4,6-bisethylamino-1,3,5-triazine
2-methylthio-4,6-bisisopropylamino-1,3,5-triazine
2-methoxy-4-ethylamino-6-isopropylamino-1,3,5-triazine
2-methoxy-4,6-bisethylamino-1,3,5-triazine
2-methoxy-4,6-bisisopropylamino-1,3,5-triazine
4-amino-6-tert.butyl-3-methylthio-4,5-dihydro-1,2,4-triazin-5-one
4-amino-6-phenyl-3-methyl-4,5-dihydro-1,2,4-triazin-5-one
4-isobutylidenamino-6-tert.butyl-3-methylthio-4,5-dihydro-1,2,4-triazin-5-one
1-methyl-3-cyclohexyl-6-dimethylamino-1,3,5-triazin-2,4-dione
3-tert.butyl-5-chloro-6-methyluracil
3-tert.butyl-5-bromo-6-methyluracil
3-isopropyl-5-bromo-6-methyluracil
3-sec.butyl-5-bromo-6-methyluracil
3-(2-tetrahydropyranyl)-5-chloro-6-methyluracil
3-(2-tetrahydropyranyl)-5,6-trimethyleneuracil
3-cyclohexyl-5,6-trimethyleneuracil
2-methyl-4-(3'-trifluoromethylphenyl)-tetrahydro-1,2,4-oxadiazine-3,5-dione
2-methyl-4-(4'-fluorophenyl)-tetrahydro-1,2,4-oxadiazine-3,5-dione
3-amino-1,2,4-triazole
1-allyloxy-1-(4-bromophenyl)-2-[1',2',4'-triazolyl-(1')]ethane (salts)
1-(4-chlorophenoxy)-3,3-dimethyl-1-(1H-1,2,3-triazol-1-yl)-butan-2-one
N,N-diallylchloroacetamide
N-isopropyl-2-chloroacetanilide
N-(but-1-yn-3-yl)-2-chloroacetanilide
2-methyl-6'-ethyl-N-propargyl-2-chloroacetanilide
2-methyl-6'-ethyl-N-ethoxymethyl-2-chloroacetanilide
2-methyl-6'-ethyl-N-(2-methoxy-1-methylethyl)-2-chloroacetanilide
2-methyl-6'-ethyl-N-(isopropoxycarbonylethyl)-2-chloroacetanilide
2-methyl-6'-ethyl-N-(4-methoxypyrazol-1-yl-methyl)-2-chloroacetanilide
2-methyl-6'-ethyl-N-(pyrazol-1-yl-methyl)-2-chloroacetanilide
2',6'-dimethyl-N-(pyrazol-1-yl-methyl)-2-chloroacetanilide
2',6'-dimethyl-N-(4-methylpyrazol-1-yl-methyl)-2-chloro-acetanilide
2',6'-dimethyl-N-(pyrazol-1-yl-methylenoxymethyl)-2-chloroacetanilide
2'-methyl-6'-ethyl-N-(pyrazol-1-yl-methylenoxymethyl)-2-chloroacetanilide
2'-methyl-6'-ethyl-N-(pyrazol-1-yl-ethylenoxymethyl)-2-chloroacetanilide
2',6'-dimethyl-N-(1,2,4-triazol-1-yl-methyl)-2-chloroacetanilide
2',6'-dimethyl-N-(3,5-dimethylpyrazol-1-yl-methyl)-2-chloroacetanilide
2',6'-dimethyl-N-(1,3-dioxolan-2-yl-methyl)-2-chloroacetanilide
2',6'-dimethyl-N-(2-methoxyethyl)-2-chloroacetanilide
2',6'-dimethyl-N-isobutoxymethyl-2-chloroacetanilide
2',6'-diethyl-N-methoxymethyl-2-chloroacetanilide
2',6'-diethyl-N-n-butoxymethyl-2-chloroacetanilide
2',6'-diethyl-N-ethoxycarbonylmethyl-2-chloroacetanilide
2',3',6'-trimethyl-N-(pyrazol-1-yl-methyl)-2-chloroacetanilide
2',3'-dimethyl-N-isopropyl-2-chloroacetanilide
2',6'-diethyl-N-(propoxyethyl)-2-chloroacetanilide
2-(2-methyl-4-chlorophenoxy-N-methoxyacetamide
2-(α-naphthoxy)-N,N-diethylpropionamide
2,2-diphenyl-N,N-dimethylacetamide
N-benzyl-N-isopropyl-trimethylacetamide
α-(3,4,5-tribromopyrazol-1-yl)-N,N-dimethylpropionamide
N-(1,1-dimethylpropynyl)-3,5-dichlorobenzamide
N-1-naphthylphthalamic acid
propionic acid 3,4-dichloroanilide cyclopropanecarboxylic acid 3,4-dichloroanilide
methacrylic acid 3,4-dichloroanilide
N-(pyrazol-1-yl-methyl)-pyrazol-1-yl-acetic acid-2,6-dimethylanilide
N-(pyrazol-1-yl-methyl)-1,2,4-triazol-1-yl-acetic acid-2,6-dimethylanilide
1-(α-2,4-dichlorophenoxypropionic acid)-3-(O-methylcarbamoyl)-anilide
1-(α-2-bromo-4-chlorophenoxypropionic acid)-3-(O-methylcarbamoyl)-anilide
2-methylpentanecarboxylic acid 3,4-dichloroanilide
5-acetamido-2,4-dimethyl-trifluoromethanesulfone anilide
5-acetamido-4-methyl-trifluoromethanesulfone anilide
N-4-methyl-5-(trifluoromethyl)-sulfonylamino-phenylacetamide
2-propionylamino-4-methyl-5-chlorothiazole
O-(methylsulfonyl)-glycolic acid N-ethoxymethyl-2,6-dimethylanilide
O-(methylaminosulfonyl)-glycolic acid N-isopropylanilide
O-(isopropylaminosulfonyl)-glycolic acid N-but-1-yn-3-yl-anilide
O-(methylaminosulfonyl)-glycolic acid hexamethyleneamide 2,6-dichlorothiobenzamide
N-[4-methoxy-6-methyl-1,3,5-triazin-2-yl-aminocarbonyl]-2-chlorobenzenesulfonamide
2,6-dichlorobenzonitrile
3,5-dibromo-4-hydroxybenzonitrile (salts)
3,5-diiodo-4-hydroxybenzonitrile (salts)
3,5-dibromo-4-hydroxy-O-2,4-dinitrophenylbenzaldoxime (salts)
3,5-dibromo-4-hydroxy-O-2-cyano-4-nitrophenylbenzaldoxime (salts) pentachlorophenol, sodium salt
2,4-dichlorophenyl-4'-nitrophenyl ether
2,4,6-trichlorophenyl-4'-nitrophenyl ether
2-fluoro-4,6-dichlorophenyl-4'-nitrophenyl ether
2-chloro-4-trifluoromethylphenyl-4'-nitrophenyl ether
2,4'-dinitro-4-trifluoromethyl-diphenyl ether
2,4-dichlorophenyl-3'-methoxy-4'-nitro-phenyl ether
2-chloro-4-trifluoromethylphenyl-3'-ethoxy-4'-nitrophenyl ether
2-chloro-4-trifluoromethylphenyl-3'-carboxy-4'-nitrophenyl ether (salts)
2-chloro-4-trifluoromethylphenyl-3'-ethoxycarbonyl-4'-nitrophenyl ether
2-chloro-4-trifluoromethylphenyl-3'-(2-fluoroethoxy)-4'-nitrophenyl ether
2-chloro-4-trifluoromethylphenyl-3'-ethoxycarbonylmethylthio-4'-nitrophenyl ether
2-chloro-4-trifluoromethyl-3'-methoxycarbonyl-4'-nitrophenyl ether
2,4,6-trichlorophenyl-3'-ethoxycarbonyl-methylthio-4'-nitrophenyl ether
2,4-dichlorophenyl-3'-methoxycarbonyl-4'-nitro-phenyl ether
2,4-dichlorophenyl-3'-carboxy-4'-nitrophenyl ether
2,4-dichlorophenyl-3'-ethoxy-4'-nitrophenyl ether
2-(3,4-dichlorophenyl)-4-methyl-1,2,4-oxadiazolidine-3,5-dione
2-(3-tert.butylcarbamoyloxyphenyl)-4-methyl-1,2,4-oxadiazolidine-3,5-dione
2-(3-isopropylcarbamoyloxyphenyl)-4-methyl-1,2,4-oxadiazolidine-3,5-dione
(4-bromophenyl)-3,4,5,9,10-pentaazatetracyclo-[5,4,1,0$^{2,60}$,$^{8,11}$]-dodeca-3,9-diene
2,3-dihydro-3,3-dimethyl-5-benzofuranyl-ethane sulfonate
2-ethoxy-2,3-dihydro-3,3-dimethyl-5-benzofuranylmethane sulfonate
2-ethoxy-2,3-dihydro-3,3-dimethyl-5-benzofuranyl-dimethylaminosulfonate
2-ethoxy-2,3-dihydro-3,3-dimethyl-5-benzofuranyl-(N-methyl-N-acetyl)-aminosulfonate
3,4-dichloro-1,2-benzisothiazole
N-4-chlorophenyl-allylsuccinimide
2-methyl-4,6-dinitrophenol (salts, esters)
2-sec.butyl-4,6-dinitrophenol (salts, esters)
2-sec.-butyl-4,6-dinitrophenol acetate
2-tert.butyl-4,6-dinitrophenol acetate
2-tert.butyl-4,6-dinitrophenol (salts)
2-tert.butyl-5-methyl-4,6-dinitrophenol (salts)
2-tert.butyl-5-methyl-4,6-dinitrophenol acetate
2-sec.amyl-4,6-dinitrophenol (salts, esters)
1-(α,α-dimethylbenzyl)-3-(4-methylphenyl)-urea
1-phenyl-3-(2-methylcyclohexyl)-urea
1-phenyl-1-benzoyl-3,3-dimethylurea
1-(4-chlorophenyl)-1-benzoyl-3,3-dimethylurea
1-(4-chlorophenyl)-3,3-dimethylurea
1-(4-chlorophenyl)-3-methyl-3-but-1-yn-3-yl-urea
1-(3,4-dichlorophenyl)-3,3-dimethylurea
1-(3,4-dichlorophenyl)-1-benzoyl-3,3-dimethylurea
1-(3,4-dichlorophenyl)-3-methyl-3-n.butylurea
1-(4-isopropylphenyl)-3,3-dimethylurea
1-(3-trifluoromethylphenyl)-3,3-dimethylurea
1-(α,α,β,β-tetrafluoroethoxyphenyl)-3,3-dimethylurea
1-(3-tert.butylcarbamoyloxyphenyl)-3,3-dimethylurea
1-(3-chloro-4-methylphenyl)-3,3-dimethylurea
1-(3-chloro-4-methoxyphenyl)-3,3-dimethylurea
1-(3-chloro-4-ethoxyphenyl)-3,3-dimethylurea
1-(3,5-dichloro-4-methoxyphenyl)-3,3-dimethylurea
1-[4-(4'-chlorophenoxy)-phenyl]-3,3-dimethylurea
1-[4-(4'-methoxyphenoxy)-phenyl]-3,3-dimethylurea
1-cyclooctyl-3,3-dimethylurea
1-(hexahydro-4,7-methanoindan-5-yl)-3,3-dimethylurea
1-[1- or 2-(3a,4,5,7,7a-hexahydro)-4,7-methanoindanyl]-3,3-di-methylurea
1-(4-fluorophenyl)-3-carboxymethoxy-3-methylurea
1-phenyl-3-methyl-3-methoxyurea
1-(4-chlorophenyl)-3-methyl-3-methoxyurea
1-(4-bromophenyl)-3-methyl-3-methoxyurea
1-(3,4-dichlorophenyl)-3-methyl-3-methoxyurea
1-(3-chloro-4-isopropylphenyl)-3-methyl-3-methoxyurea
1-(3-chloro-4-methoxyphenyl)-3-methyl-3-methoxyurea
1-(3-tert.butylphenyl)-3-methyl-3-methoxyurea
1-(2-benzthiazolyl)-1,3-dimethylurea
1-(2-benzthiazolyl)-3-methylurea
1-(5-trifluoromethyl-1,3,4-thiadiazolyl)-1,3-dimethylurea
1-(4-benzyloxyphenyl)-3-methyl-3-methoxyurea
imidazolidin-2-one-1-carboxylic acid isobutylamide
1-[4-(2-(p-methylphenyl)-ethoxy)-phenyl]-3-methyl-3-methoxyurea
1,2-dimethyl-3,5-diphenylpyrazolium-methylsulfate
1,2,4-trimethyl-3,5-diphenylpyrazolium-methylsulfate
1,2-dimethyl-4-bromo-3,5-diphenylpyrazolium-methylsulfate
1,3-dimethyl-4-(3,4-dichlorobenzoyl)-5-(4-methylphenylsulfonyloxy)-pyrazole
1-acetyl-3-anilino-4-methoxycarbonyl-5-methylpyrazole
3-anilino-4-methoxycarbonyl-5-methylpyrazole
3-tert-butylamino-4-methoxycarbonyl-5-methylpyrazole 2,3,5-trichloropyridinol-(4)
2-chloro-3,5-diiodo-4-acetoxypyridine
1-methyl-3-phenyl-5-(3'-trifluoromethylphenyl)-pyridone-(4)
1-methyl-4-phenylpyridinium chloride
1,1-dimethylpyridinium chloride
3-phenyl-4-hydroxy-6-chloropyridazine
1,1'-dimethyl-4,4'-dipyridylium-di(methylsulfate)
1,1'-di-(3,5-dimethylmorpholine-carbonylmethyl)-4,4'-dipyridylium dichloride
1,1'-ethylene-2,2'-dipyridylium dibromide
2-chlorophenoxyacetic acid (salts, esters, amides)
4-chlorophenoxyacetic acid (salts, esters, amides)
2,4-dichlorophenoxyacetic acid (salts, esters, amides)
2,4,5-trichlorophenoxyacetic acid (salts, esters, amides)
2-methyl-4-chlorophenoxyacetic acid (salts, esters, amides)
3,5,6-trichloro-2-pyridinyl-oxyacetic acid (salts, esters, amides)
methyl α-naphthoxyacetate
ethyl 2-[4-(5'-bromopyridyl-2-oxy)-phenoxy]-propionate
ethyl 2-[4-(5'-iodopyridyl-2-oxy)-phenoxy]-propionate
n-butyl 2-[4-(5'-idopyridyl-2-oxy)-phenoxy]-propionate
2-(2-methylphenoxy)-propionic acid (salts, esters, amides)
2-(4-chlorophenoxy)-propionic acid (salts, esters, amides)
ethyl (2-methyl-4-chlorophenoxy)-thioacetate
2-(2,4-dichlorophenoxy)-propionic acid (salts, esters, amides)
2-(2,4,5-trichlorophenoxy)-propionic acid (salts, esters, amides)
2-(2-methyl-4-chlorophenoxy)-propionic acid (salts, esters, amides)
methyl 2-[4-(4'-chlorophenoxymethyl)-phenoxy]-propionate
4-(2,4-dichlorophenoxy)-butyric acid (salts, esters, amides)
4-(2-methyl-4-chlorophenoxy)-butyric acid (salts, esters, amides)
cyclohexyl-3-(2,4-dichlorophenoxy)-acrylate
9-hydroxyfluorenecarboxylic acid-(9) (salts, esters)
2,3,6-trichlorophenylacetic acid (salts, esters)
4-chloro-2-oxobenzothiazolin-3-yl-acetic acid (salts, esters)
3-[1(N-ethoxyamino)-propylidene]-6-ethyl-3,4-dihydro-2-H-pyran-2,4-dione
3-[1-(N-allyloxyamino)-propylidene]-6-ethyl-3,4-dihydro-2-H-pyran-2,4-dione
2-[1-(N-allyloxyamino)-propylidene]-5,5-dimethylcyclohexane-1,3-dione (salts)
2-[1-(N-allyloxyamino)-butylidene]-5,5-dimethylcyclohexane-1,3-dione (salts)
2-[1-(N-allyloxyamino)-butylidene]-5,5-dimethyl-4-methoxycarbonyl-cyclohexane-1,3-dione (salts)
2-[1-(N-ethoxyamino)-butylidene]-5-(2-ethylthiopropyl)-3-hydroxy-cyclohex-2-en-1-one (salts)
2-[1-(N-ethoxamino)-butylidene]-5-(2-phenylthiopropyl)-3-hydroxy-cyclohex-2-en-1-one (salts)
gibelleric acid (salts)
disodium methylarsonate
monosodium salt of methylarsonic acid
N-phosphonomethyl-glycine (salts)
N,N-bis-(phosphonomethyl)-glycine (salts)
2-chloroethyl 2-chloroethanephosphonate
ammonium-ethyl-carbamoyl-phosphonate
di-n-butyl-1-n-butylamino-cyclohexyl-phosphonate
trithiobutylphosphite
O,O-diisopropyl-5-(2-benzosulfonylaminoethyl)-phosphorodithioate
2,3-dihydro-5,6-dimethyl-1,4-dithiin-1,1,4,4-tetraoxide
5-tert.butyl-3-(2,4-dichloro-5-isopropoxyphenyl)-1,3,4-oxadiazolone-(2)
4,5-dichloro-2-trifluoromethylbenzimidazole (salts)
1,2,3,6-tetrahydropyridazine-3,6-dione (salts)
succinic acid mono-N-dimethylhydrazide (salts)
(2-chloroethyl)-trimethylammonium chloride
(2-methyl-4-phenylsulfonyl)-trifluoromethanesulfone anilide
1,1-dimethyl-4,6-diisopropyl-5-indanyl ethyl ketone
2-[1-(2,5-dimethylphenyl)-ethylsulfonyl]-pyridine-N-oxide
2-(3'-trifluoromethylphenyl)-4H-3,1-benzoxazin-4-one
2-(2-thienyl)-4H-3,1-benzoxazin-4-one
2-phenyl-4H-3,1-benzoxazin-4-one
sodium chlorate
ammonium thiocyanate
calcium cyanamide.

It may also be useful to apply the mixture according to the invention, alone or in combination with other herbicides, in admixture with other crop protection agents, e.g., agents for combating pests or phytopathogenic fungi or bacteria. The compounds may also be mixed with solutions of mineral salts used to remedy nutritional or trace element deficiencies. To initiate the herbicidal action, wetting agents, spreader-stickers and non-phytotoxic oils and oil concentrates may be added.

The influence of the herbicidal diphenyl ethers of the formula I on the growth of unwanted and crop plants is illustrated in greenhouse experiments and experiments in the open.

As comparative agents, the prior art active ingredients

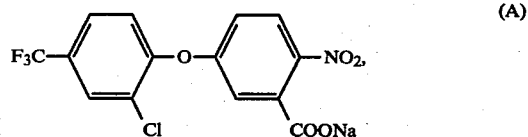

(A)

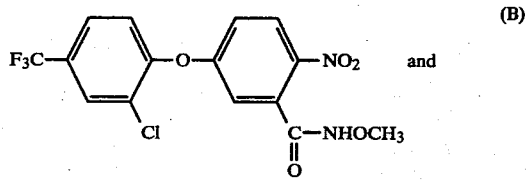

(B)

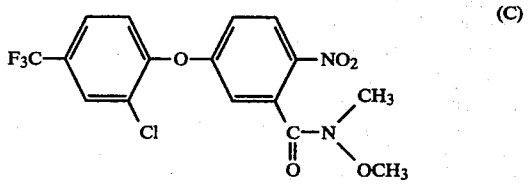

(C)

were used.

The following plants were employed in the experiments: Amaranthus spp., *Chenopodium album, Euphorbia geniculata, Galium aparine,* Ipomoea spp., Lamium spp., Polygonum spp., *Raphanus raphanistrum, Solanum nigrum, Sinapis alba, Triticum aestivum,* and *Sinapis arvensis.*

The vessels employed for the greenhouse experiments were plastic flowerpots having a volume of 300 cm³, and which were filled with a sandy loam containing about 1.5% humus. The seeds of the test plants were sown shallow, and separately, according to species.

In the preemergence treatment, the active ingredients were applied to the surface of the soil as a suspension or emulsion in water by spraying through finely distributing nozzles. The amount of active ingredient applied in this treatment was equivalent to 3.0 kg/ha.

After the agents had been applied, the vessels were lightly sprinkler-irrigated to induce germination and growth. Transparent plastic covers were then placed on the vessels until the plants had taken root. The cover ensured uniform germination of the plants, insofar as this was not impaired by the chemicals.

For the postemergence treatment, the plants were first grown in the vessels to a height of from 3 to 15 cm, depending on growth form, before being treated. The rice plants used for postemergence application were grown in a peat-enriched substrate. For this treatment, either plants which had been sown directly in the pots and grown there were selected, or plants which had been grown separately as seedlings and transplanted to the experiment vessels a few days before treatment. The amount of active ingredient applied in this treatment varied, depending on the active ingredient, and was either 0.06, 0.125, 0.25 or 3.0 kg/ha. No cover was placed on the vessels in this treatment.

The pots were set up in the greenhouse-species from warmer areas at from 20° to 35° C., and species from moderate climates at 10° to 25° C. The experiments were run for from 2 to 4 weeks. During this period, the plants were tended and their reactions to the various treatments assessed. The scale used for assessment was 0 to 100, 0 denoting no damage or normal emergence, and 100 denoting nonemergence or complete destruction of at least the visible plant parts.

The experiments in the open were run on small plots, the soil being a sandy loam having a pH of about 6 and containing 1 to 1.5% humus. The crop plants were sown in rows for the postemergence treatment. The weed flora was natural. The compounds were emulsified or suspended in water as distribution medium, and applied by means of a motor-driven plot spray mounted on a tractor. At the time of application, the winter cereal was in the tillering stage and was, on average, 15 cm high. The weeds were in the rosette stage, and thus had several true leaves, branchings or whorls of leaves, and were about 3 to 10 cm high.

The experiments show that the compounds have, on postemergence application, a better herbicidal action than the comparative agents on a number of unwanted plants. In addition, some of the compounds according to the invention are better tolerated by certain crop plants. When the compounds are applied preemergence, a herbicidal action is also observed.

In investigations into selective herbicidal action on postemergence application in the greenhouse, active ingredient no. 1 has, at low application rates, a much better herbicidal action and is much better tolerated by crop plants than comparative agents A, B and C used at the higher application rates.

Active ingredients nos. 2, 3, 8 and 9 also had, on postemergence application in the greenhouse, a good action on unwanted plants.

Compounds nos. 1 and 9 also had a good action on preemergence application in the greenhouse.

In the experiments in the open, active ingredient no. 1 had, on postemergence application at low rates, a very good action on various broadleaved weed species, and was also well tolerated (with slight, temporary, leaf scorching) by winter wheat.

We claim:

1. A diphenyl ether of the formula

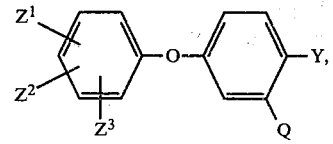

where $Z^1$, $Z^2$ and $Z^3$ independently of one another are each hydrogen, halogen, nitro, cyano, carboxyl, alkyl of 1 to 4 carbon atoms, or haloalkyl, alkoxy, haloalkoxy, alkylmercapto, haloalkylmercapto, alkylsulfinyl, haloalkylsulfinyl, alkylsulfonyl or haloalkylsulfonyl where alkyl is in each case of 1 to 4 carbon atoms, Y is hydrogen, halogen, cyano or nitro and Q is —CO—NA—OR$^1$, where A is hydrogen, alkyl of 1 to 4 carbon atoms, a metal ion or an unsubstituted or trialkyl substituted ammonium ion and R$^1$ is carboxyalkyl, alkoxycarbonylalkyl or carbamylalkyl of not more than 10 carbon atoms.

2. A diphenyl ether of the formula I as claimed in claim 1, where $Z^1$, $Z^2$ and $Z^3$ are hydrogen or, in the 2-, 4- and 6-, or 3-, 4- and 6-, or 3-, 4- and 5-positions on the phenyl ring, independently of one another are each halogen or haloalkyl or haloalkylmercapto, each of 1 to 4 carbon atoms, Y is hydrogen, halogen or nitro and Q is —CO—NA—OR$^1$, where A is hydrogen or alkyl of 1 to 4 carbon atoms and R$^1$ is carboxyalkyl, alkoxycarbonylalkyl or carbamylalkyl of not more than 6 carbon atoms.

3. A diphenyl ether of the formula I as claimed in claim 1, wherein $Z^1$, $Z^2$ and $Z^3$ are hydrogen or, in the 2-, 4- and 6-, or 3-, 4- and 5-positions, independently of one another are each halogen or haloalkyl of 1 to 4 carbon atoms, Y is hydrogen or nitro and Q is —CO—NA—OR$^1$, where A is hydrogen and R$^1$ is alkoxycarbonylalkyl or carbamylalkyl of not more than 6 carbon atoms.

4. 3-(2'-Chloro-4'-trifluoromethylphenoxy)-6-nitrobenz-hydroxamic acid-(α-methoxycarbonyl)-ethyl ether.

5. 3-(2'-Chloro-4'-trifluoromethylphenoxy)-benzhydroxamic acid-(α-methoxycarbonyl)-methyl ether.

6. 3-(2'-Chloro-4'-trifluoromethylphenoxy)-benzhydroxamic acid-(α-methoxycarbonyl)-ethyl ether.

7. 3-(2'-Chloro-4'-trifluoromethylphenoxy)-6-nitrobenz-hydroxamic acid-(α-methoxycarbonyl)-methyl ether.

8. A process for combating the growth of unwanted plants, wherein the unwanted plants, or the area to be kept free of unwanted plant growth, are treated with a herbicidally effective amount of a diphenyl ether of the formula I as claimed in claim 1.

9. A herbicide containing inert additives and, as active ingredient, a diphenyl ether of the formula

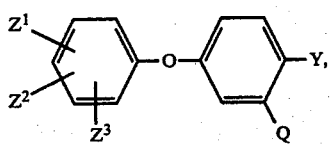

where $Z^1$, $Z^2$ and $Z^3$ independently of one another are each hydrogen, halogen, nitro, cyano, carboxyl, alkyl of 1 to 4 carbon atoms, or haloalkyl, alkoxy, haloalkoxy, alkylmercapto, haloalkylmercapto, alkylsulfinyl, haloalkylsulfinyl, alkylsulfonyl or haloalkylsulfonyl where alkyl is in each case of 1 to 4 carbon atoms, Y is hydrogen, halogen, cyano or nitro and Q is —CO—NA—OR$^1$, where A is hydrogen, alkyl of 1 to 4 carbom atoms, a metal ion or an unsubstituted or trialkyl substituted ammonium ion and R$^1$ is carboxyalkyl, alkoxycarbonylalkyl or carbamylalkyl of not more than 10 carbon atoms.

* * * * *

UNITED STATES PATENT AND TRADEMARK OFFICE
CERTIFICATE OF CORRECTION

PATENT NO. : 4,426,220
DATED : January 17, 1984
INVENTOR(S) : Adolf PARG et al.

It is certified that error appears in the above-identified patent and that said Letters Patent is hereby corrected as shown below:

Claims 4 and 7, column 22. There should only be one space between benz-hydroxamic acid.

Claim 9, line 6, column 24, carbom should be spelled carbon.

On the title page:
IN FOREIGN PAT. DOCUMENTS 54-151943 should read 79 151943

Signed and Sealed this

Twenty-ninth Day of May 1984

[SEAL]

Attest:

GERALD J. MOSSINGHOFF

Attesting Officer

Commissioner of Patents and Trademarks